(12) United States Patent
Simon

(10) Patent No.: US 8,145,319 B1
(45) Date of Patent: Mar. 27, 2012

(54) METHODS AND DEVICES FOR TREATMENT OF OSTEONECROSIS OF THE FEMORAL HEAD WITH CORE DECOMPRESSION

(75) Inventor: Bruce J. Simon, Mountain Lakes, NJ (US)

(73) Assignee: EBI, LLC, Parsippany, NJ (US)

( * ) Notice: Subject to any disclaimer, the term of this patent is extended or adjusted under 35 U.S.C. 154(b) by 1142 days.

(21) Appl. No.: 11/247,521

(22) Filed: Oct. 11, 2005

(51) Int. Cl.
*A61N 1/18* (2006.01)
(52) U.S. Cl. .......................................................... 607/51
(58) Field of Classification Search .................... 607/50, 607/51; 424/424, 484; 623/20.35, 22.21; 628/23.11; 606/80, 56, 60, 96, 916
See application file for complete search history.

(56) References Cited

U.S. PATENT DOCUMENTS

| | | | |
|---|---|---|---|
| 3,918,440 A | 11/1975 | Kraus | |
| 4,026,304 A | 5/1977 | Levy | |
| 4,430,999 A | 2/1984 | Brighton et al. | |
| 4,461,300 A | 7/1984 | Christensen | |
| 4,506,674 A | 3/1985 | Brighton et al. | |
| 4,549,547 A | 10/1985 | Brighton et al. | |
| 4,782,833 A | 11/1988 | Einhorn et al. | |
| 4,889,111 A * | 12/1989 | Ben-Dov | 606/56 |
| 5,030,236 A | 7/1991 | Dean | |
| 5,738,521 A | 4/1998 | Dugot | |
| 6,112,122 A * | 8/2000 | Schwardt et al. | 607/51 |
| 6,292,699 B1 | 9/2001 | Simon et al. | |
| 6,778,861 B1 | 8/2004 | Liebrecht et al. | |
| 7,146,222 B2 * | 12/2006 | Boling | 607/116 |
| 2003/0135214 A1 * | 7/2003 | Fetto et al. | 606/72 |
| 2005/0049640 A1 | 3/2005 | Gurtner et al. | |
| 2005/0075680 A1 * | 4/2005 | Lowry et al. | 607/45 |
| 2006/0200150 A1 * | 9/2006 | Ilomaki et al. | 606/73 |

OTHER PUBLICATIONS

Steinberg, Marvin E., et al. Treatment of Avascular Necrosis of the Femoral Head by a Combination of Bone Grafting, Decompression, and Electrical Stimulation. Clin Orthop Relat Res. Jun. 1984; (186):137-53.*
M.E. Steinberg et al., "Osteonecrosis of the Femoral Head: Results of Core Decompression and Grafting With and Without Electrical Stimulation," *Clinical Orthopaedics and Related Research*, No. 249, Dec. 1989, pp. 199-208.
R.K. Aaron et al., "Electrical Stimulation of Osteonecrosis of the Femoral Head," *Seminars in Arthroplasty*, vol. 2, No. 3, Jul. 1991, pp. 214-221.
R.K. Aaron, "Osteonecrosis: Etiology, Pathophysiology, and Diagnosis," *The Adult Hip*, © 1998, Chapter 28, pp. 451-466, Lippincott-Raven Publishers, Philadelphia.
D. Ciombor, "Biologically Augmented Core Decompression for the Treatment of Osteonecrosis of the Femoral Head," *Techniques in Orthopaedics*, vol. 16, No. 1, Mar. 2001, pp. 32-38.
M.E. Steinberg et al., "Core Decompression With Bone Grafting for Osteonecrosis of the Femoral Head," *Clinical Orthopaedics and Related Research*, No. 386, May 2001, pp. 71-78.

(Continued)

*Primary Examiner* — Carl H Layno
*Assistant Examiner* — Jeremiah Kimball
(74) *Attorney, Agent, or Firm* — William F. Bahret

(57) ABSTRACT

Methods and devices for treatment of osteonecrosis of the femoral head with core decompression include a dowel adapted for placement into a core decompression channel of a femoral head. A cathode at the distal end of the dowel provides electrical stimulation of bone growth in the femoral head. A method of treating osteonecrosis of the femoral head involves placing a dowel having a cathode thereon into a core decompression channel of a femoral head in a state of osteonecrosis. Electrical current is supplied to the cathode for electrical stimulation of bone growth in the femoral head.

19 Claims, 3 Drawing Sheets

OTHER PUBLICATIONS

A.R. Vaccaro, "The Role of the Osteoconductive Scaffold in Synthetic Bone Graft," *Orthopedics Supplement*, vol. 25, No. 5, May 2002, pp. s571-s578.

OsteoStem Cortical Lok literature, circa 2003, 15 pages.

EBI OsteoGen Surgical Procedure, undated, 19 pages.

Brighton, C.T., "Present and Future of Electrically Induced Osteogenesis," in *Clinical Trends in Orthopaedics*, Ed. L.R. Straub et al., pp. 1-15, 1982.

* cited by examiner

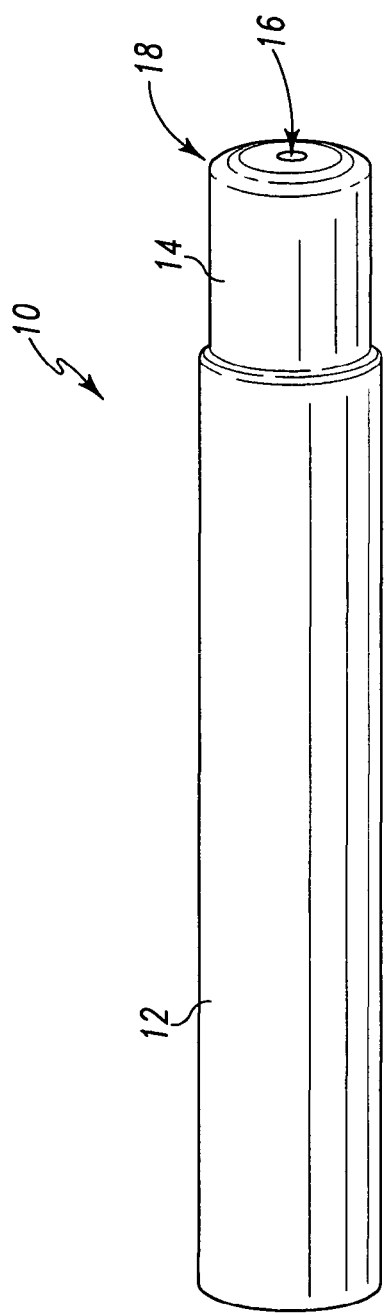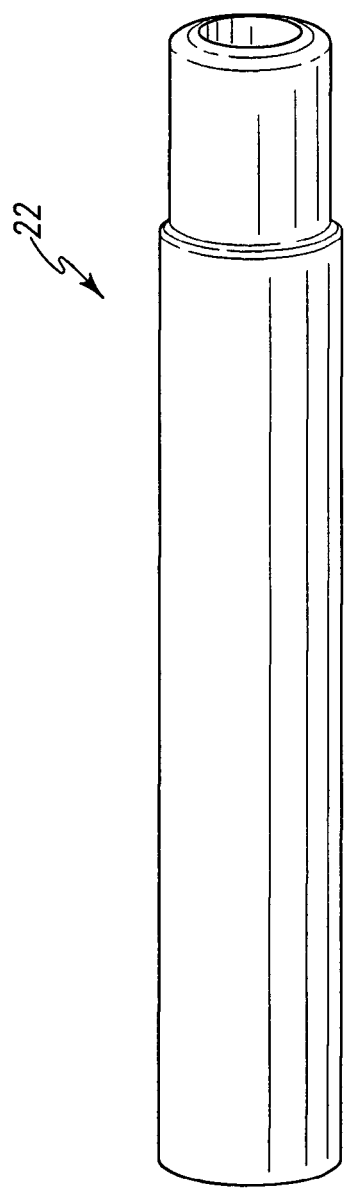
Fig. 1
Fig. 2

METHODS AND DEVICES FOR TREATMENT OF OSTEONECROSIS OF THE FEMORAL HEAD WITH CORE DECOMPRESSION

BACKGROUND OF THE INVENTION

This invention relates to stimulation of bone growth in the femoral head, and particularly to devices and methods used to treat osteonecrosis of the femoral head.

Osteonecrosis, or avascular necrosis (AVN), of the femoral head is a serious medical condition which afflicts about 20,000 people per year. Due to poor blood circulation to the head of the femur, bone necrosis occurs. As the body tries to remove the necrotic bone by osteoclastic resorption, the head of the femur weakens and eventually collapses, leading to total hip replacement.

Core decompression is a common procedure used to treat and retard progression of osteonecrosis of the femoral head that involves cutting a channel from the lateral cortex, just beneath the flare of the trochanter, into the necrotic bone of the femoral head. Various trials have been conducted to determine the effectiveness of core decompression on the treatment of osteonecrosis of the femoral head, with some including the use of bone grafting and electrical stimulation to study their effects on treatment.

In core decompression procedures utilizing electrical stimulation in addition to bone grafting to treat osteonecrosis of the femoral head, direct current bone growth stimulators have been used in conjunction with normal cancellous bone material removed from the trochanteric region and distal neck to improve the effectiveness of the treatment. In these procedures, the cathode electrodes of the stimulators have been wrapped around bone chips removed from the core decompression channel and sutured into place for placement into the core decompression channel.

Cathode placement devices are known to be used with direct current electrical stimulators to provide control of placement of the direct current electrical stimulator cathode and to alleviate migration of the cathode. An example of a cathode placement device is the EBI OsteoStim® Cortical-Lok bone dowel. The OsteoStim CorticalLok bone dowel is designed for placement across bone fractures to stimulate bone fusion, having distal and proximal portions designed to hold the intermediate shaft portion in position across a bone fracture.

There remains a need for a cathode placement device for the treatment of osteonecrosis of the femoral head that is adapted for use in conjunction with core decompression surgical procedures.

SUMMARY OF THE INVENTION

The present invention provides new methods and devices for treatment of osteonecrosis of the femoral head. According to one aspect of the invention, a dowel adapted for placement into a core decompression channel of a femoral head has a cathode at the distal end thereof for electrical stimulation of bone growth in the femoral head.

A new method according to the present invention involves placing a dowel having a cathode thereon into a core decompression channel of a femoral head in a state of osteonecrosis, and supplying electrical current to the cathode for electrical stimulation of bone growth in the femoral head.

According to a further aspect of the present invention, a device for treatment of osteonecrosis of the femoral head includes a resorbable dowel adapted for placement into a core decompression channel of a femoral head to provide an osteogenic environment.

In broad terms, the invention provides a new indication for a dowel with a cathode for electrical bone growth stimulation: The method comprises providing such a dowel and indicating its use for treatment of the osteonecrosis of the femoral head.

The objects and advantages of the present invention will be more apparent upon reading the following detailed description in conjunction with the accompanying drawings.

BRIEF DESCRIPTION OF THE DRAWINGS

FIG. 1 is a perspective view of one embodiment of a dowel for treatment of osteonecrosis of the femoral head according to the present invention.

FIG. 2 is a perspective view of another embodiment of a dowel for treatment of osteonecrosis of the femoral head according to the present invention.

DESCRIPTION OF PREFERRED EMBODIMENTS

Figure 3:
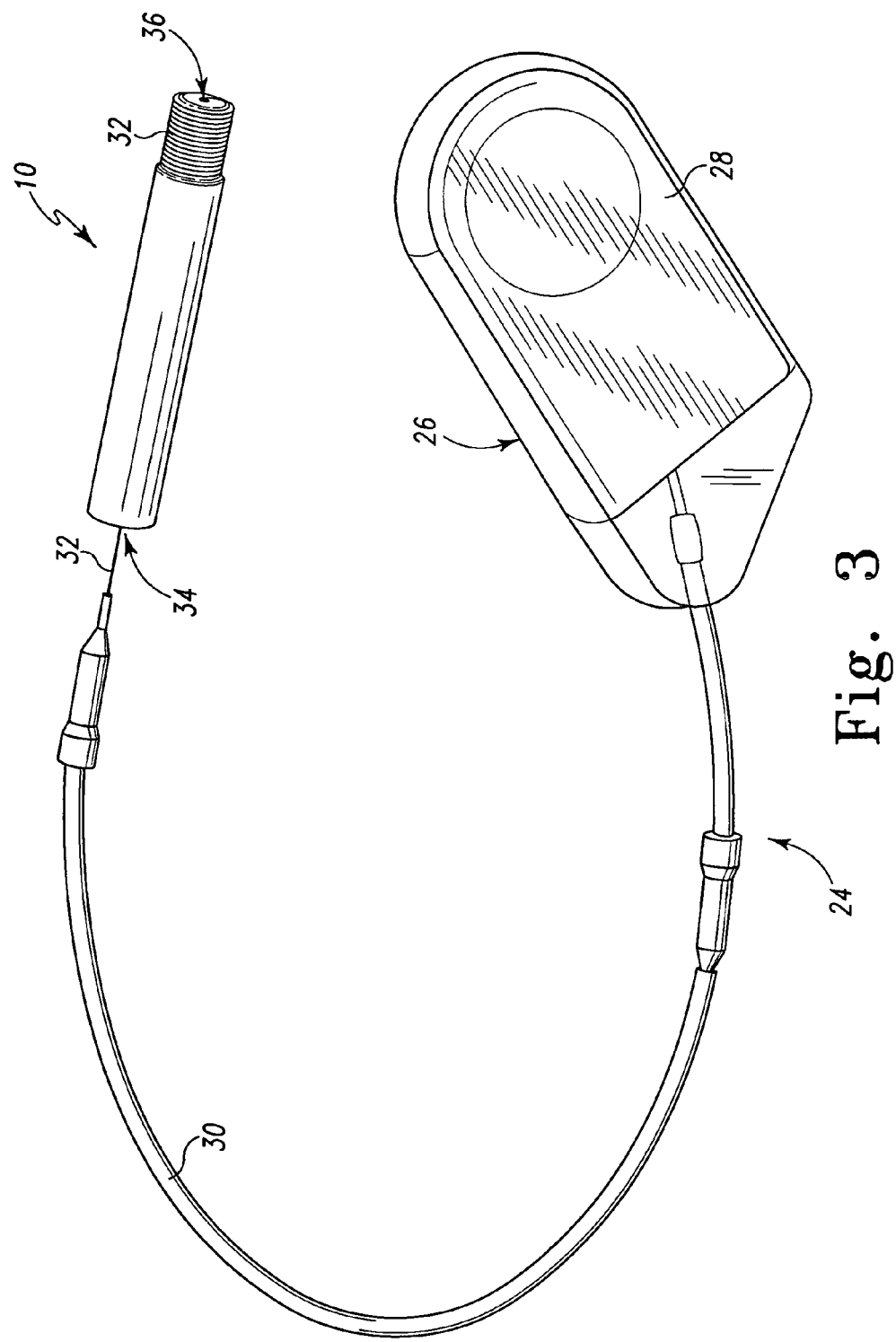
FIG. 3 shows an implantable bone growth stimulator with the dowel of FIG. 1.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

FIG. 1 shows an embodiment of a dowel 10 according to the present invention, typically having a length in the range of about 4-8 centimeters (cm), preferably about 6 cm. The dowel 10 has a proximal end 12, preferably having an outer diameter in the range of about 6-12 millimeters (mm), preferably about 8-10 mm, and has a reduced-diameter distal portion 14, preferably about 2 mm smaller in diameter, to maintain substantially the same outer diameter of the dowel 10 when a cathode electrode of a bone growth stimulator is wrapped around the distal portion 14. One suitable cathode is titanium wire having a diameter of about 1 mm, insulated through the dowel, with an un-insulated exposed length of about 12 cm wrapped around the distal portion. A bore 16, preferably oriented along the longitudinal axis of the dowel 10, is provided as a path for the cathode wire. The bore 16 may be sized slightly larger than a cathode wire to provide a snug fit for the cathode wire and to maintain overall dowel strength, or, alternatively, may be larger, as shown in FIG. 2, reducing the overall mass of the dowel 22 to promote faster resorption and facilitate bone ingrowth.

In other alternative embodiments, the dowel may have an external longitudinal groove for carrying a cathode wire from the proximal end of the dowel to the distal end of the dowel, or the dowel may have an external threaded portion in place of the reduced-diameter distal portion 14, with the major diameter of the threads equal to the outer diameter of the proximal end 12 and with the cathode wire in the roots of the threads. Alternatively, the cathode electrode may be internally concentrated within the dowel at the distal end. Further, the dowel could have a concentration of carbon embedded in a spiral or helical pattern about the dowel that could be used as an electrically conductive path in place of using a cathode wire.

The dowel 10, 22 may be made of allograft bone, such as cortical bone, or, more preferably may be made of a resorbable material such as commercially available Lactosorb from Biomet, Inc. or Bioplex from Interpore Cross International, Inc, or from calcium phosphate ($CaPO_4$) or calcium sulphate ($CaSO_4$), for example. Utilizing resorbable materials such as Lactosorb or Bioplex allows manufacture of the dowel 10, 22 without need of allograft bone and avoids the cost and complications associated with the use of allograft bone.

Referring to FIG. 3, there is illustrated an example of an implantable bone growth stimulator 24, such as OsteoGen™ surgically implanted bone growth stimulator from EBI, contemplated for use with dowels 10, 22 comprising a current generator 26 having a housing 28 that is electrically conductive and comprises an anode, an insulated lead 30, and a cathode electrode 32. A battery and control circuitry are disposed within the housing and serve to deliver an electrical current through bone tissue between the anode of the housing and the cathode. Such electrical current is effective in stimulating the growth of bone at a site in the vicinity of the cathode, according to well-known principles.

FIG. 3 illustrates how the cathode electrode 32 of the bone growth stimulator 24 is used with the dowel 10 of FIG. 1. The cathode electrode 32 is preferably introduced into bore 16 by way of the proximal opening 34, where it may be advanced through the dowel 10 to the distal opening 36 of the shaft 16. The cathode electrode 32 is then wrapped about the reduced-diameter distal portion 14 of the dowel 10 so that the cathode electrode 32 is concentrated at the distal end 18 of the dowel 10. The dowel 10 may then be used as a placement device to place the cathode electrode 32 of the bone growth stimulator 24 in the core decompression channel of a subject's femur, and to hold the cathode electrode 32 adjacent to necrotic bone of the femoral head.

In one preferred method of treating osteonecrosis of the femoral head, the dowels 10, 22 of the present invention may be used in conjunction with a core decompression procedure to provide an osteogenic environment within the femoral head and to partially bear weight placed upon the femoral head. The method involves placing a dowel adapted to fit into a core decompression channel, such as dowels 10 and 22, into a core decompression channel, in place of, or in conjunction with bone material removed during cutting of the core decompression channel, to promote bone growth.

Figure 4:
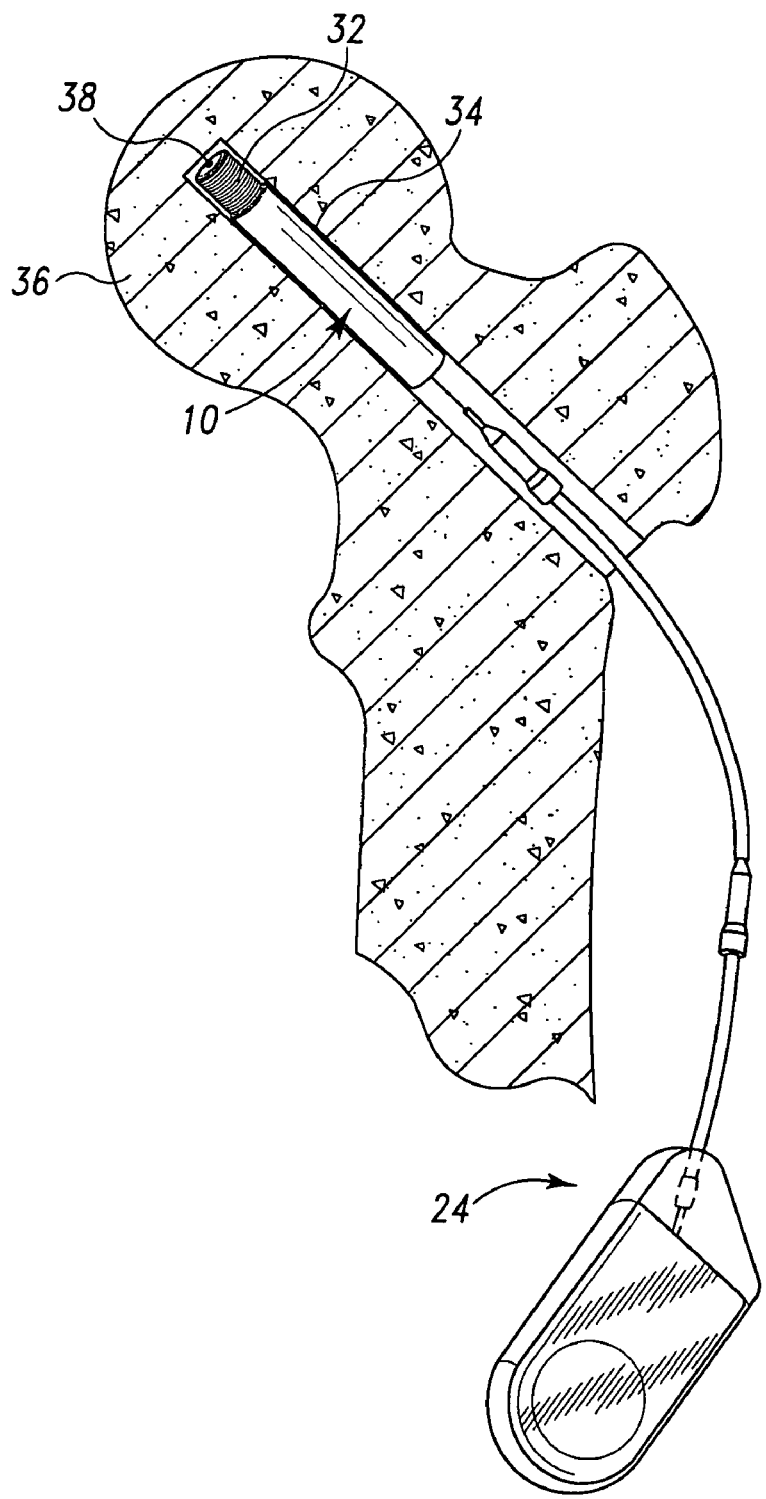
FIG. 4 illustrates placement of the device of FIG. 4 in a core decompression channel of a subject's femoral head.

Another preferred method of treating osteonecrosis of the femoral head involves utilizing the dowels 10, 22 of the present invention as a cathode placement device to improve efficacy of the treatment. The cathode electrode 32 of a bone growth stimulator 24 may be wrapped about dowels 10, 22, as previously described, so that the cathode electrode 32 is concentrated at the distal end 18 of the dowel 10. The dowel 10 may then be inserted into a core decompression channel 34 of a subject's femoral head 36, as shown in FIG. 4, oriented so that the distal end 18 of the dowel 10 is adjacent the distal end 38 of the core decompression channel 34. The bone growth stimulator 24 may then be used to supply direct current in the range of 20-200 microamperes (μA) to the cathode electrode 32, with 100 μA being a more preferred current level to stimulate bone growth within femoral head 36.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A device for treatment of osteonecrosis of a femoral head, comprising:
   a preformed, hollow, resorbable polymer dowel adapted for placement into a core decompression channel of a femoral head, said dowel having a proximal end and a distal end, and having an open-ended bore therethrough along the long axis of said dowel; and
   an electrically conductive cathode wire introduced into said bore at the proximal end thereof and advanced through said dowel and out its distal end for providing electrical stimulation of bone growth in the femoral head.

2. The device of claim 1, wherein said dowel has a maximum outer diameter of from about 6 mm to about 12 mm, and a length of from about 4 cm to about 8 cm.

3. A device for treatment of osteonecrosis of a femoral head, comprising:
   a preformed, hollow, resorbable polymer dowel adapted for placement into a core decompression channel of a femoral head, said dowel having a proximal end and a distal end; and
   a cathode at said distal end of said dowel for providing electrical stimulation of bone growth in the femoral head;
   wherein said preformed, hollow, resorbable polymer dowel has an open-ended bore therethrough, along the long axis of said dowel, and wherein said cathode comprises an electrically conductive wire with an outer diameter less than one-fourth the outer diameter of the distal end of said dowel and of length substantially greater than that of said dowel, and extends through said bore and out the distal end thereof where it is exposed to the environment external to said device.

4. The device of claim 3, wherein said distal end is smaller in outer diameter than said proximal end, wherein said cathode comprises electrically insulated wire inside said bore within said resorbable polymer dowel, and wherein said cathode comprises uninsulated wire wrapped around said distal end of said dowel and exposed to the environment external to said device.

5. A method of treating osteonecrosis of a femoral head, comprising:
   placing a preformed, hollow dowel having a cathode wire therein and thereon into a core decompression channel of a femoral head in a state of osteonecrosis, wherein said dowel is made of a resorbable polymer and has an open-ended bore therethrough along its long axis, and wherein said wire is introduced into said bore at the proximal end thereof and is advanced therethrough and out its distal end; and
   supplying an electrical current to said cathode for electrical stimulation of bone growth in the femoral head.

6. The method of claim 5, wherein said dowel has an outer diameter of from about 6 mm to about 12 mm, and a length of from 4 cm to about 8 cm.

7. The method of claim 6, wherein said dowel has a length of from about 6 cm to about 8 cm.

8. The method of claim 5, wherein said electrical current is direct current in the range of approximately 20-200 μA.

9. The method of claim 8, wherein said cathode wire includes a single uninsulated helical cathode portion formed around the distal end of said dowel, and wherein said electrical current is non-pulsed direct current at a level of approximately 100 µA through said single uninsulated helical cathode portion.

10. The method of claim 5, wherein said cathode is concentrated at one end of said dowel for positioning adjacent osteonecrotic bone.

11. The method of claim 10, wherein said dowel has an open-ended bore therethrough, along the long axis of said dowel, and wherein said cathode extends through said bore and out the distal end thereof where it is exposed to the environment external to said device.

12. A method of treating osteonecrosis of a femoral head of a patient comprising: fabricating a preformed, hollow resorbable polymer dowel with a cathode wire for electrical bone grown stimulation, wherein said wire is introduced into said dowel at the proximal end thereof and is advanced longitudinally therethrough and out of the distal end thereof and is wrapped around said distal end; providing said dowel and said wire to a user to stimulate the femoral head of said patient; and indicating the use of said dowel for treatment of osteonecrosis of the femoral head.

13. The method of claim 12, wherein said dowel has an outer diameter of from about 6 mm to about 12 mm, and a length of from 4 cm to about 8 cm.

14. The method of claim 12, wherein said electrical current is direct current in the range of approximately 20-200 µA.

15. The method of claim 14, wherein said portion of said cathode wire wrapped around said distal end of said dowel is uninsulated, and wherein said electrical current is non-pulsed direct current at a level of approximately 100 µA through said uninsulated cathode wire portion wrapped around said distal end of said dowel.

16. The method of claim 12, wherein said electrical stimulation is further characterized by concentrating said cathode at one end of said dowel for positioning adjacent osteonecrotic bone.

17. The method of claim 16, wherein said dowel has an open-ended bore therethrough, along the long axis of said dowel, and wherein said cathode extends through said bore and out the distal end thereof where it is exposed to the environment external to said device.

18. A method of fabricating an electrified dowel for treatment of osteonecrosis of a femoral head, comprising:
forming a hollow, resorbable polymer dowel sized and shaped for placement into a core decompression channel of a femoral head, said dowel having a proximal end, a distal end, and an open-ended bore therethrough along the long axis thereof; and
introducing an electrically conductive cathode wire into said bore at the proximal end thereof and advancing said wire through said dowel and out its distal end for providing electrical stimulation of bone growth in the femoral head.

19. The method of claim 18, further comprising:
forming a helical coil around said distal end of said dowel with the portion of said electrically conductive cathode wire extending out of said distal end.

* * * * *